United States Patent [19]
Yerkes

[11] 3,964,167
[45] June 22, 1976

[54] DISPOSABLE TOOTH SHADE GUIDE

[76] Inventor: John G. Yerkes, P.O. Box 502, Bloomfield, Conn. 06002

[22] Filed: Oct. 24, 1974

[21] Appl. No.: 517,481

[52] U.S. Cl. .................................................. 32/71
[51] Int. Cl.² ........................................ A61C 13/00
[58] Field of Search ............................ 32/71, 40 R

[56] References Cited
UNITED STATES PATENTS

| | | | |
|---|---|---|---|
| 1,265,581 | 5/1918 | Zurbrigg | 32/71 |
| 1,518,608 | 12/1924 | Short | 32/71 |
| 2,789,353 | 4/1957 | Biggs | 32/71 |
| 3,748,741 | 7/1973 | Yerkes | 32/71 |

*Primary Examiner*—Robert Peshock

[57] ABSTRACT

A disposable tooth shade guide is provided operable for use by a dentist in determining by comparison the particular shade of an artificial tooth that may be substituted for a natural tooth of a patient. The tooth shade guide includes an elongated holder of generally rectangular configuration. At one end thereof the holder has an artificial tooth secured thereon. The artificial tooth embodies the configuration of a natural tooth and is colored a predetermined shade selected from the various colors which natural teeth most commonly are found to have. The artificial tooth is mounted on the holder by means of a pin which is suitably fastened to the rear of the artificial tooth so as to project outwardly therefrom substantially at right angles to the major axis of the artificial tooth. The pin is passed through an opening provided therefor at the aforementioned one end of the holder. A lock ring is passed over the free end of the pin after the latter is passed through the holder thereby locking the artificial tooth to the holder, yet permitting the former to pivot relative to the latter. A cap is detachably mounted over the artificial tooth on the holder. The cap is suitably dimensioned and configured so as to be receivable on the artificial tooth with a snap fit. In addition, the cap is preferably provided with an outwardly extending tab operable for use in removing the cap from engagement with the artificial tooth and also as a means upon which an identifying letter, numeral, symbol, etc. may be applied to distinguish one cap from another. The cap is colored a predetermined shade whereby when mounted on the artificial tooth the cap is effective to alter the basic color of the artificial tooth to produce a variation in the shade thereof.

8 Claims, 6 Drawing Figures

DISPOSABLE TOOTH SHADE GUIDE

BACKGROUND OF THE INVENTION

A practice which is commonly followed by many dentists when there is a need to prepare a tooth for a crown or to extract a patient's tooth is to suggest to the patient the possibility of replacing the natural tooth with an artificial tooth.

In those instances wherein the natural tooth is to be replaced after extraction by an artificial tooth, or is being prepared for a crown, the dentist commonly preparatory to extracting the tooth or before or after preparation for a crown will attempt to match the coloration of the natural tooth to that of an artificial tooth which will then thereafter be substituted therefor, or will be employed in preparing the crown. This is accomplished conventionally by determining by comparison the particular shade of an artificial tooth that will match the coloration of the natural tooth. Because of the fact that the natural tooth has not yet been extracted, or prepared for a crown, the aforedescribed comparison must be made within the interior of the patient's mouth. One method which is very often used to perform the comparison is to position an artificial tooth having a known coloration adjacent to the natural tooth in the patient's mouth for purposes of comparing the coloration of the artificial tooth with that of the natural teeth. It should be readily apparent that there are a number of factors which will influence the determination of this comparison such as for example, the lighting which is available in the room, the shadows which are cast in the patient's mouth, the extent to which the natural teeth transmit light, etc.

As derived from a reference to the prior art, there have been provided heretofore a variety of different types of devices which are intended to be employed in connection with the performance of a comparison of the coloration of an artificial tooth with that of a natural tooth for which the former is to be substituted. In accordance with the teachings of the prior art, most commonly a set is provided of artificial teeth which differ in coloration one from another. Moreover, each of the artificial teeth in a set is suitably supported on its own individual holder. By way of illustration, reference is had in this regard particularly to U.S. Pat. Nos. 1,207,895; 2,479,543; and 2,805,478. In U.S. Pat. No. 1,207,895, there is shown a set of artificial teeth embodying different colorations which are each supported on an individual mounting. The latter mountings are in turn received in a holder which is generally rectangular in configuration. There is shown in U.S. Pat. No. 2,479,543 a set of artificial teeth wherein the teeth which are each of different coloration are formed integrally with a mounting. A circular holder is provided for purposes of grouping the teeth with a set i.e., for supporting the mountings thereon. U.S. Pat. No. 2,805,478 shows still another embodiment of a tooth shade guide. The latter guide consists of a holder having a generally curved configuration. There is affixed to the holder for pivotal movement relative thereto a multiplicity of radially extending arms. Each of the latter arms at the free end thereof carries an artificial tooth. The artificial teeth which together constitute a set thereof differ one from another insofar as concerns their coloration.

Having determined through the employment of a tooth shade guide such as one of those which has been described in the preceding paragraph the coloration which the artificial tooth should possess, most often the dentist himself will not actually manufacture the artificial tooth. Rather, this is a task which is performed by a dental laboratory. More specifically, the dentist instructs the dental laboratory as to the coloration which the artificial tooth should have in order that it may produce an artificial tooth which will match that of the natural tooth which is being extracted. The manner in which the dentist conveys to the dental laboratory the information regarding the coloration which it is desired that the artificial tooth have is by identifying the coloration by number. Namely, each of the various artificial teeth which are included in a set thereof that forms a tooth shade guide are designated by means of an identifying number. Moreover, both the dentist and the dental laboratory possess the same type of tooth shade guide. Therefore, the dentist need merely tell the dental laboratory the specific type of tooth shade guide which he has utilized for purposes of making the comparison determination and the identifying number of the particular tooth in the set of artificial teeth which together form the tooth shade guide which has been selected as a result of the comparison determination. Thereupon, the dental laboratory need merely refer to that particular artificial tooth in the tooth shade guide which bears the specified identifying number provided thereto by the dentist in order to produce an artificial tooth that embodies the desired coloration.

Down through the years, a number of modifications have been made in the construction of prior art forms of tooth shade guides. By and large these modifications have been directed to attempts to faciliate the manner in which the tooth shade guide is used. Namely, changes have been sought to be made in the configuration of the individual mounting which carries the artificial tooth as well as in the nature of the configuration thereof so as to be able to more easily position the artificial tooth within the patient's mouth in juxtaposed relation to the natural tooth with which the comparison is to be made. The result has been to produce tooth shade guides wherein the mountings are formed of different types of material such as for example, resilient materials or wherein the configuration of the mountings has been modified so as to embody one or more suitably placed bends operable to facilitate the entry of the mounting into the patient's mouth.

Notwithstanding all of the above referenced efforts to effect improvements in the construction of tooth shade guides, one particular difficulty encountered in the employment of a tooth shade guide has had very little attention focused thereon. More specifically, as will be readily apparent from a reference to the prior art, it is only possible to include a limited number of artificial teeth in each tooth shade guide. Consequently, the dentist is limited in the number of different shades of artificial teeth from which he can select in making his comparison determination as to the coloration which the artificial tooth must have in order to match that of the natural tooth for which it is to serve as a replacement. At best therefore, the result is that the coloration selected represents only an approximation of the actual coloration which the artificial tooth should have. In order to achieve a closer approximation to the true color, the dentist in his instructions to the dental laboratory will select the coloration of the artificial tooth in the tooth shade guide which appears to come closest to the shade of the natural tooth and often will request the dental laboratory to provide an artificial tooth which is somewhat darker, more yellow, etc. in shade than the specified artificial tooth. Obviously, this poses a dilemma to the dental laboratory insofar as concerns their determination as to how much darker or how much more yellow, etc. the artificial tooth should be made. The most readily apparent manner of obviating the aforedescribed problem is to increase the number of artificial teeth which are embodied in a tooth shade guide. The difficulty with this proposal however, is that to do so requires providing a holder which is sufficiently large in dimensions so as to be capable of supporting the increased number of artificial teeth. From a practical standpoint, the bulkiness of such a holder as well as the added expense incurred in the manufacture of such a holder and in the manufacture of the added number of artificial teeth have combined to render this proposal undesirable. Of course, it is readily apparent that a holder need not be provided for the mountings which carry the artificial teeth. Namely, a tooth shade guide could be provided which consisted of a multiplicity of artificial teeth which are loose. Such an approach has also proven to be undesirable in that it has been found that the individual mountings are easily lost or misplaced so as not to be readily available when needed. This stems from the fact that each of the artificial teeth including its individual mounting is relatively small in size. Thus, it has been found that a need exists to provide a tooth shade guide which is capable of increasing the number of different shades of artificial teeth from which the dentist is capable of selecting in making his comparison determination as to the coloration of the artificial tooth which most closely corresponds to the coloration of the natural tooth. Moreover, there exists a need to provide such a tooth shade guide which does not suffer from the disadvantages possessed by the tooth shade guides which have been proposed heretofore in an attempt to overcome the problem which dentists have experienced in arriving at an accurate selection of the coloration which the artificial tooth should have.

Accordingly, it is an object of the present invention to provide a novel and improved tooth shade guide operable for use by a dentist in determining by comparison the particular shade of an artificial tooth that may be substituted for a natural tooth of a patient.

It is another object of the present invention to provide such a tooth shade guide which is operable to afford a larger selection of shades of coloration of artificial teeth which can be matched to the coloration of a natural tooth.

A further object of the present invention is to provide such a tooth shade guide wherein the artificial tooth is provided with a covering which is effective to alter the basic color of the artificial tooth to produce a variation in the shade thereof.

A still further object of the present invention is to provide such a tooth shade guide wherein the covering consists of a detachable cap which is mountable with a snap fit on the artificial tooth.

Yet another object of the present invention is to provide such a tooth shade guide which employs artificial teeth and mountings which are presently commercially available as well as, it is expected, those which will become available in the future.

Yet still another object of the present invention is to provide such a tooth shade guide which is easy to employ, yet is relatively inexpensive to manufacture.

SUMMARY OF THE INVENTION

It has now been found that the foregoing and related objects can be readily attained in a tooth shade guide which is operable for use by a dentist in determining by comparison the particular shade of an artificial tooth that may be substituted for a natural tooth of a patient. The tooth shade guide includes an elongated holder of generally rectangular configuration. At one end thereof the holder has an artificial tooth secured thereon. The artificial tooth embodies the configuration of a natural tooth and is colored a predetermined shade selected from the various colors which natural teeth are most commonly found to have. Mounting means are provided for fastening the artificial tooth to the holder. A covering is provided which is capable of being affixed to the artificial shade tooth sample. The covering is operable when positioned on the artificial tooth to alter the basic color of the artificial tooth to produce a variation in the shade thereof.

In accord with the preferred embodiment of the invention, the artificial tooth is mounted on the holder by means of a pin which is suitably fastened to the rear of the artificial tooth so as to project outwardly therefrom substantially at right angles to the major axis of the artificial tooth. The pin is passed through an opening provided therefor at the aforementioned one end of the holder. A lock ring is passed over the free end of the pin after the latter is passed through the holder thereby locking the artificial tooth to the holder, yet permitting the former to pivot relative to the latter. The covering consisting of a cap is detachably mounted over the artificial tooth on the holder. The cap is suitably dimensioned and configured so as to be receivable on the artificial tooth with a snap fit. In addition, the cap is preferably provided with an outwardly extending tab operable for use in removing the cap from engagement with the artificial tooth and also as a means upon which an identifying letter, numeral, symbol, etc. may be applied to distinguish one cap from another.

DETAILED DESCRIPTION OF THE ILLUSTRATED EMBODIMENT

Figure 1:
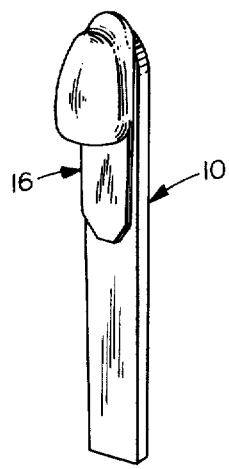
FIG. 1 is a perspective view of a tooth shade guide member constructed in accordance with the present invention.
Figure 2:
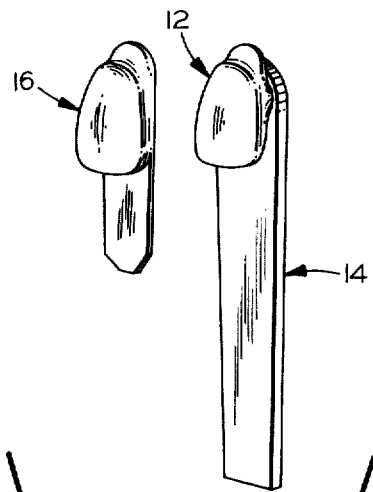
FIG. 2 is an exploded perspective view of a tooth shade guide member constructed in accordance with the present invention.

Referring now to the drawings and more particularly FIGS. 1 and 2 thereof, there is depicted therein a tooth shade guide member, generally designated by reference numeral 10. The tooth shade guide member 10 is capable of being employed by a dentist in determining by comparison the particular shade of an artificial tooth that may be substituted for a natural tooth of a patient. The tooth shade guide member 10 is intended to be employed as a part of a set thereof wherein the set in turn constitutes a tooth shade guide. However, inasmuch as all of the tooth shade guide members which are included in a tooth shade guide are substantially similar in construction, it has not been deemed necessary for purposes of obtaining an understanding of the present invention to illustrate in the drawings and describe herein the multiplicity of tooth shade guide members 10 which together function to form a tooth shade guide. Rather, it has been deemed sufficient merely to illustrate in the drawings one such tooth shade guide member 10. As will be again referred to herein subsequently, essentially the only difference which exists between one and another of the tooth shade guide members in a set thereof resides in the nature of the coloration of the artificial tooth, although there may be some slight change provided in the configuration of the artificial tooth for purposes of depicting selected ones of the different forms of natural teeth which are commonly found embodied in a human's mouth such as for example, molars, etc.

As best understood with reference to FIG. 2 of the drawings, the tooth shade guide member 10 consists of an artificial tooth 12 which is suitably affixed to a mounting, i.e., holder 14. A cap 16 is detachably mountable on the artificial tooth 12. The artificial tooth 12 is suitably dimensioned and configured so as to resemble a natural tooth both in size and in appearance. In this regard, the artificial tooth 12 may be formed from any suitable non-toxic synthetic material which resembles in texture and hardness that of a natural tooth. Moreover, the artificial tooth 12 is colored a predetermined shade which is selected from one of the various colors which natural teeth are most commonly found to have. In the drawings, the artificial tooth 12 is depicted as embodying one particular type of configuration. However, it is to be understood that the external configuration of the artificial tooth 12 could be altered, if so desired, so as to provide the artificial tooth 12 with an external appearance which more closely resembles one of the other types of teeth which are found most commonly to be embodied in the mouth of a human being, without departing from the essence of the invention. Similarly, it is to be understood that the coloration of the artificial tooth 12 will vary from one tooth shade guide member 10 to another within a given tooth shade guide.

The holder 14 as best understood with reference to FIG. 2 of the drawings comprises a member which in accord with the illustrated embodiment of the invention is depicted as embodying a substantially rectangular configuration. The holder 14 is preferably made of a suitable non-toxic plastic material which is capable of being inserted into a patient's mouth without causing injury to the patient. Moreover, the length of the holder 14 is selected to be such as to provide a suitable accessible portion thereon by which the holder 14 may be grasped so as to facilitate the movement of the tooth shade guide member 10 for purposes of adjusting the position thereof in a patient's mouth relative to the natural tooth the coloration of which is sought to be matched.

Figure 3:
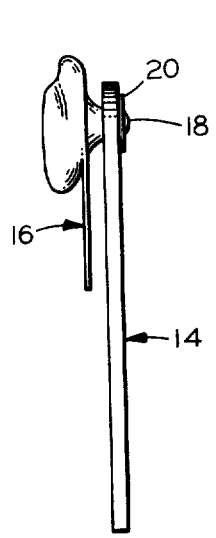
FIG. 3 is a side elevational view of a tooth shade guide member constructed in accordance with the present invention.
Figure 4:
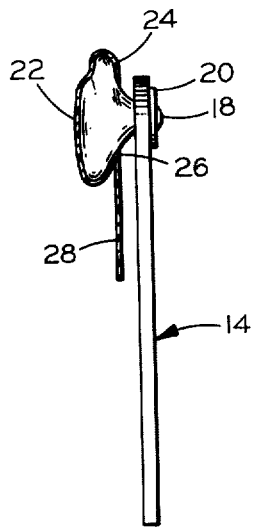
FIG. 4 is a side elevational view partially in section of a tooth shade guide member constructed in accordance with the present invention.

Turning now to FIGS. 3 and 4 of the drawings, it is readily understood with reference thereto that the artificial tooth 12 is provided with a pin 18. In accord with the preferred embodiment of the invention, the pin 18 comprises a separate member. Obviously, however, if so desired, the pin 18 could take the form of a button-like projection formed as an integral part of the artificial tooth 12 without departing from the essence of the present invention. The pin 18 has one end thereof fixedly secured to the rear face of the artificial tooth 12 whereby the pin 18 projects outwardly from the rear of the artificial tooth 12 substantially at right angles to the major axis thereof. For purposes of mounting the artificial tooth 12 on the holder 14, the free end of the pin 18 is passed through an opening (not shown) provided for this purpose at one end of the holder 14. Therafter, a lock ring 20 is preferably positioned on the free end of the pin 18 whereby the lock ring 20 is operable to lock the artificial tooth 12 on the holder 14, while yet permitting the artificial tooth 12 to move relative to the holder 14. The fact that the artificial tooth 12 is movable relative to the holder 14 has been schematically illustrated in FIG. 5 of the drawings wherein the artificial tooth 12 is depicted in solid lines occupying the normal position thereof relative to the holder 14 and in broken lines a multiplicity of alternate positions which the artificial tooth 12 may bear relative to the holder 14. The reason for supporting the artificial tooth 12 on the holder 14 so as to enable the former to move relative to the latter is to facilitate the locating of the artificial tooth 12 in juxtaposed relation to a natural tooth in a patient's mouth to assist the dentist in performing the comparison of the coloration of the artificial tooth 12 with that of the natural tooth which is to be replaced with an artificial tooth. Although in accord with the illustrated embodiment of the invention, the artificial tooth 12 is shown captured on the holder 14 through the use of the lock ring 20 it is to be understood that some other form of locking means such as for example, a cotter pin, etc. could be substituted therefor without departing from the essence of the invention.

Figure 5:
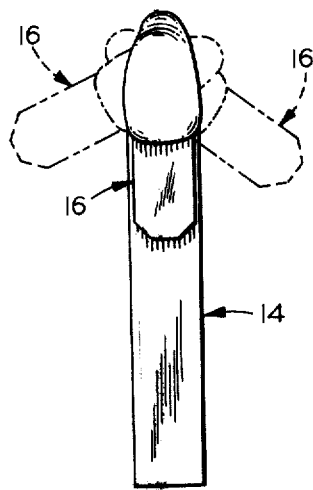
FIG. 5 is a front elevational view of a tooth shade guide member constructed in accordance with the present invention, illustrating in solid lines the position which the artificial tooth normally bears relative to the holder and in broken lines a multiplicity of alternate positions which the artificial tooth may bear relative to the holder.

Referring again to FIG. 2 of the drawings as well as to FIG. 4 thereof, the cap 16 as illustrated therein is suitably dimensioned and configured so as to be detachably mounted on the artificial tooth 12 whereby the cap 16 functions as a covering for the face of the artificial tooth 12. More specifically, the cap 16 comprises a member having a first portion 22 thereof which corresponds in dimensions and configuration to the front face of the artificial tooth 12. The portion 22 is provided at one end thereof with a first inwardly turned flange 24 and at the other end with a second inwardly turned flange 26. The distance measured between the flange 24 and the flange 26 is purposely chosen so as to be less than the length of the front face of the artificial tooth 12 measured along the major axis thereof. Consequently, when the cap 16 is mounted on the artificial tooth 12 it will remain positioned thereon. To mount the cap 16 on the artificial tooth 12, the former is positioned on the latter so that the flange 24 overlies the upper end as viewed with reference to FIG. 5 of the drawings of the artificial tooth 12. Thereafter, by exerting a pressing force on the portion 22 of the cap 16 adjacent the flange 26 thereof the latter can be snapped over the bottom edge of the artificial tooth 12 so that the flange 26 bears the relationship to the artificial tooth 12 which is shown in FIG. 5 of the drawings. To facilitate the removal of the cap 16 from the artificial tooth 12, the former is preferably provided with a tab 28 which is formed integrally as a part of the cap 16 extending outwardly of the flange 26 thereof. With the cap 16 positioned on the artificial tooth 12, the former may be detached from the latter simply by grasping the end of the tab 28 and pulling upwardly thereon causing the flange 26 to slide over the bottom end of the artificial tooth 12. It is of course to be understood however that the snap fit could be accomplished in other ways such as by providing the cap 16 with side flanges whereby by first positioning one of the side flanges of the cap 16 in overlying relation with the artificial tooth 12 and then applying a pressing force to the portion 22 of the cap 16, the latter may be snapped onto the artificial tooth 12 by means of a side to side snap fit.

Continuing with a description of the cap 16, the latter is formed of a suitable non-toxic synthetic material characterized by sufficient resiliency to permit the cap 16 to be snapped over the face of the artificial tooth 12. In addition, the cap 16 is preferably formed from a translucent material which may be of different colors. Consequently, by virtue of the latter characteristic of the material from which the cap 16 is formed, the latter when mounted on the artificial tooth 12 is effective to alter the color of the artificial tooth 12 so that the coloration of the artificial tooth 12 with the cap 16 positioned thereon differs from that of the artificial tooth 12 without the cap 16 thereon. As a result, through the use of the cap 16 it is possible to double the number of shades of coloration of artificial teeth which the dentist has to select from in employing a given tooth shade guide for purposes of performing a comparison as to which coloration of an artificial tooth most nearly duplicates the coloration of the natural tooth which is to be replaced by an artificial tooth or for which a crown is being prepared. In this regard, it is to be noted that all of the tooth shade guide members 10 in a given tooth shade guide embody substantially identical constructions whereby the cap 16 will fit on the artificial tooth 12 on any one of the tooth shade guide members 10.

There will now be set forth a description of the manner in which the tooth shade guide member 10 is employed. In this connection, it is to be understood that the tooth shade guide member 10 comprises only one of a multiplicity thereof which together function as a set that in turn forms a tooth shade guide. Bearing the preceding in mind, it will be assumed that the dentist seeks to match the coloration of an artificial tooth with that of a natural tooth which is to be extracted and replaced by an artificial tooth or which is being prepared for a crown. Thus, the dentist begins by selecting from the tooth shade guide the tooth shade guide member 10 which embodies an artificial tooth 12 that appears to possess the coloration which most closely approximates the coloration of the natural tooth. Having selected a particular tooth shade guide member 10 from the tooth shade guide, the former is positioned within the patient's mouth so that the artificial tooth 12 is located in juxtaposed relation to the natural tooth. With the artificial tooth 12 so placed relative to the natural tooth, the dentist proceeds to compare the coloration of the artificial tooth 12 vis-a-vis the coloration of the natural tooth. This trial and error procedure is repeated until the tooth shade guide member 10 carrying the artificial tooth 12 whose coloration most nearly duplicates the coloration of the natural tooth is found. Most often, it is found that the coloration of the artificial tooth 12 which is selected as a result of the aforedescribed comparison determination by the dentist does not duplicate exactly the coloration of the natural tooth. In accord with the present invention therefore, for purposes of obtaining a closer approximation of the coloration of the natural tooth, the tooth shade guide member 10 which has been selected by the aforedescribed procedure is removed from the patient's mouth. Thereafter, the cap 16 is positioned on the artificial tooth 12 and the tooth shade guide member 10 is repositioned within the patient's mouth so that the artificial tooth 12 with the cap 16 supported thereon is in juxtaposed relation to the natural tooth so that a comparison may once again be performed between the former and the latter. As described previously hereinabove, the cap 16 when positioned on the artificial tooth 12 is effective to alter the color of the artificial tooth 12 to produce a variation in the shade thereof. The degree to which the coloration of the artificial tooth 12 is varied obviously will depend on the extent to which the material from which the cap 16 is formed is colored. Assuming that the coloration provided by the combined cap 16 and artificial tooth 12 is determined to most closely duplicate the coloration of the natural tooth, this fact must be conveyed to the dental laboratory which in turn will produce the artificial tooth which will be substituted for the natural tooth after the latter has been extracted from the patient's mouth or for which a crown is being prepared. There are several ways in which the desired information can be transmitted to the dental laboratory. More specifically, if the dental laboratory has a supply of caps 16 on hand, the dentist need only advise the dental laboratory as to the particular type of tooth shade guide which the dentist has employed in making the comparison, the identifying number which the particular tooth shade guide member 10 which has been selected bears, and the fact that a cap 16 suitably identified such as by number, letter, symbol, etc. should be placed on the artificial tooth 12 of the tooth shade guide member 10 to obtain the desired coloration. On the other hand, if the dental laboratory does not have any caps 16 available, the dentist need only identify for the dental laboratory the type of tooth shade guide which was employed, the identifying number of the particular tooth shade guide member 10 which was selected, and send the actual cap 16 which he employed to the dental laboratory whereat the cap 16 can be placed on the artificial tooth 12 of the tooth shade guide member 10 by someone at the dental laboratory preparatory to preparing the artificial tooth. Inasmuch as the caps 16 are very inexpensive to produce, the latter procedure is very often found to be most desirable. It should be readily apparent from the above that the cap 16 cooperates with the artificial tooth 12 of a tooth shade guide member 10 to provide a simple, inexpensive and efficient means of increasing the number of shades of coloration of artificial teeth which the dentist has at his disposal for purposes of determining the coloration of a natural tooth by comparing the coloration of an artificial tooth thereto. Moreover, although for purposes of the above discussion, the cap 16 has been described as being formed of a translucent colored material whereby when placed on an artificial tooth 12 it is effective to vary the shade of the coloration which the latter appears to have, it is to be understood that the dentist could be provided with several caps 16 which differ one from another in the degree to which they are translucent or insofar as concerns their coloring so that each of these caps 16 when placed on the artificial tooth 12 will be effective to vary the coloration of the artificial tooth 12 to a different extent whereby a multiplicity of different shades of coloration is obtainable depending on which one of the caps 16 is positioned on the artificial tooth 12.

Figure 6:
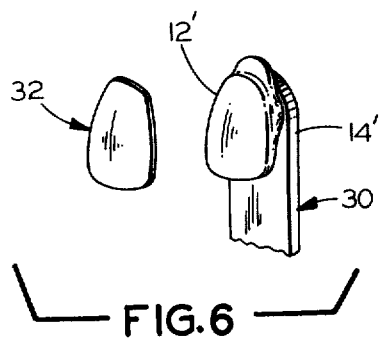
FIG. 6 is an exploded perspective view of a portion of another embodiment of a tooth shade guide member constructed in accordance with the present invention.

Referring now to FIG. 6 of the drawings, there is illustrated therein another embodiment of a tooth shade guide member, generally designated by reference numeral 30, constructed in accordance with the present invention. Inasmuch as the tooth shade guide member 30 is similar in construction to the tooth shade guide member 10, the components of the latter which find correspondence with the components of the former have been identified in FIG. 6 of the drawings by means of the same numerals which were applied to the components of the tooth shade guide member 10 in FIGS. 1–5 but with a prime being added thereto. Thus, as shown in FIG. 6 of the drawings, the tooth shade guide member 30 consists of an artificial tooth 12' which is suitably affixed to a mounting, i.e., holder 14'. Although not visible in FIG. 6, it is to be understood that the artificial tooth 12' is preferably mounted on the holder 14' for pivotal movement relative thereto by means of a pin and lock ring arrangement such as that utilized in the tooth shade guide member 10. Namely, as was described hereinabove in connection with the discussion of the nature of the construction of the tooth shade guide member 10 and as illustrated particularly in FIGS. 3 and 4 of the drawings, the artificial tooth 12' is provided with a pin, one end of which is secured to the rear face of the artificial tooth 12' with the other end thereof being passed through an opening provided therefor in the holder 14'. Moreover, the artificial tooth 12' is maintained on the holder 14' through the use of a lock ring which embodies the same construction as the lock ring 20. The essential difference between the tooth shade guide member 30 of FIG. 6 and the tooth shade guide member 10 of FIGS. 1–5 resides in the fact that whereas the latter includes a cap 16 the former does not. More particularly, in place of the cap 16 a covering 32 is employed. The covering 32 which is preferably formed of a suitable non-toxic synthetic material that is translucent is suitably dimensioned and configured so as to correspond to the dimensions and configuration of the front face of the artificial tooth 12'. The covering 32 is intended to be employed in the same manner as has been described hereinabove for the cap 16 of the tooth shade guide member 10, namely, to provide a means which is effective to alter the coloration of the artificial tooth supported thereon so as to produce a variation in the shade thereof. Inasmuch as it is desired to be able to remove the covering 32 from the face of the artificial tooth 12', the former is preferably affixed to the latter through the use of a pressure sensitive adhesive. More specifically, although not depicted in FIG. 6 of the drawings in the interest of maintaining clarity of illustration therein, it is to be understood that there is provided on the inner surface of the covering 32 a layer of pressure sensitive adhesive. The latter is operable when the covering 32 is placed on the front face of the artificial tooth 12' and pressure applied thereto to fasten the covering 32 to the artificial tooth 12'. In addition, after the comparison determination as to coloration has been performed by the dentist, the covering 32 may be removed from the latter simply by grasping one corner of the covering 32 and peeling the latter from the face of the artificial tooth 12'.

The tooth shade guide member 30 is intended to be employed in the same fashion as has been set forth hereinabove in connection with the description of the tooth shade guide member 10 except insofar as concerns positioning the covering 32 on an artificial tooth rather than the cap 16. More specifically, the same procedural steps which are followed with the tooth shade guide member 10 up to the point whereat the cap 16 is to be applied thereto are also performed in using the tooth shade guide member 30. However, when the dentist has arrived at the point whereby he has selected one particular tooth shade guide member 30 from the tooth shade guide and desires if possible to achieve a closer approximation to the coloration of the natural closer tooth, the covering 32 is positioned on the front face of the artificial tooth 12' and a further comparison is made by the dentist between the coloration of the natural tooth and that produced with the covering 32 affixed to the artificial tooth 12'. Insofar as concerns conveying the information regarding the coloration of the artificial tooth which most closely approximates that of the natural tooth from the dentist to the dental laboratory, the same two means which were described hereinabove in connection with the cap 16 may be employed with the covering 32, namely, if the dental laboratory has on hand one or more coverings 32 they are instructed to produce an artificial tooth which has the same coloration as that provided by positioning the covering 32 on the artificial tooth 12' of a particular tooth shade guide member 30, or the particular covering 32 which was utilized by the dentist in making his comparison determination as to coloration may be sent to the dental laboratory where it is available for positioning on the particular tooth shade guide member 30. With further regard to the covering 32, it is to be understood that like the cap 16 the dentist may be provided with several coverings 32 which differ one from another insofar as concerns the degree to which they are translucent or colored whereby when placed on an artificial tooth 12', they are each effective to vary the shade of coloration produced by the artificial tooth 12' to a different extent.

Although two embodiments of a tooth shade guide member constructed in accordance with the present invention have been shown in the drawings and described hereinabove, it is to be understood that modifications in the construction thereof may be made thereto by those skilled in the art without departing from the essence of the invention. In this connection, some of the modifications which can be made in the tooth shade guide member have been alluded to hereinabove while others will become readily apparent to those skilled in the art when exposed to the present description and illustration of the construction of the tooth shade guide members 10 and 30. For example, as was set forth previously hereinabove, a variety of different types of materials may be employed in the manufacture of the artificial tooth, the holder, the cap and/or the covering which together function to comprise a tooth shade guide member. In this regard, the characteristics which the material selected should possess are that it be non-toxic so as to be capable of being placed in a patient's mouth, that it be provided with a sufficiently smooth surface so as to minimize the possibility that it will be the cause of injury to the patient's mouth, and that the material be sufficiently durable so as not to be harmed by the moist environment to which it is exposed when placed in a patient's mouth. In addition, obviously the artificial tooth could be mounted on the holder through the use of some means other than the pin and lock ring arrangement which have been depicted in the drawings, without departing from the essence of the invention. Moreover, modifications could obviously be made to the external configuration of the artificial tooth and/or the holder without departing from the essence of the invention. Furthermore, if found desirable, the tab 28 with which the cap 16 is provided could be eliminated therefrom without departing from the essence of the invention. Similarly, the configuration of the cap 16 could be modified so that the cap 16 more completely encompasses the entire outer surfaces of the artificial tooth. Also, obviously, the covering 32 could be secured to the outer face of the artificial tooth through some means other than providing the former with a layer of pressure sensitive adhesive. In order to increase the number of selections of shades of coloration which are available, it is also possible to provide a second set of caps which are slightly larger in dimension that the cap 16 shown in the drawings and which are constructed so as to be capable of being snapped over the cap 16 after the latter in turn has been mounted on the artificial tooth 12. Thus, by utilizing a second cap which is placed over the cap 16, a second variation in the coloring of the artificial tooth 12 is obtained, i.e., the color of the artificial tooth 12 being first varied as a result of the placement of the cap 16 thereon and then a second time by virtue of the placement of the second cap over the cap 16. Another means by which the coloration of the artificial tooth 12 may be varied is by spraying from a can, etc. a suitable non-toxic substance onto the surface of the cap 16 so that a relatively thin, film-like layer is caused to be deposited thereon. The latter layer when so applied to the surface of the cap 16 is then effective to produce a variation in the nature of the coloration of the artificial tooth 12, when the cap 16 is thereafter mounted on the latter tooth 12.

Thus, it can be seen that the present invention provides a novel and improved tooth shade guide member operable for use by a dentist in determining by comparison the particular shade of an artificial tooth that may be substituted for a natural tooth of a patient. Moreover, in accord with the present invention a tooth shade guide member is provided which is operable to afford a larger selection of shades of coloration of artificial teeth which can be matched with the coloration of a natural tooth. The tooth shade guide member of the present invention includes an artificial tooth which is capable of being provided with a covering which is effective to alter the basic color of the artificial tooth to produce a variation in the shade thereof. Furthermore, in accord with the present invention a tooth shade guide member has been provided wherein the covering applied to the artificial tooth consists of a detachable cap which is mountable on the artificial tooth with a snap fit. Also, a tooth shade guide member has been provided in accord with the present invention which employs therein artificial teeth and mountings of the type which are presently commercially available. Finally, in accord with the present invention a tooth shade guide member has been provided which is easy to employ, yet is relatively inexpensive to manufacture.

Having thus described the invention, I claim:

1. A tooth shade guide member operable for use by a dentist in determining by comparison the particular shade of an artificial tooth that may be substituted for a natural tooth of patient comprising:
   a. a tooth-simulating member having at least a front face dimensioned and configured to provide the appearance of a natural tooth, said tooth-simulating member being formed of a non-toxic material and having a preselected visible coloration;
   b. an elongated mounting member operable as a support for said tooth-simulating member and formed of a non-toxic material;
   c. means pivotably mounting said tooth-simulating member adjacent one end of said mounting member for pivotal movement relative thereto; and
   d. translucent cover means detachably secured on said front face of said tooth-simulating member, said cover means being formed of a non-toxic material transmitting light therethrough, said cover means when mounted on said front face of said tooth-simulating member having a coloration effective to alter said visible coloration of said tooth-simulating member so as to produce a variation in the shade of the apparent coloration of said tooth-simulating member from that seen when said cover means is dismounted from said front face of said tooth-simulating member.

2. The tooth shade guide member as set forth in claim 1 wherein said mounting is generally rectangular in configuration.

3. The tooth shade guide member as set forth in claim 1 wherein said mounting means includes a pin having one end thereof affixed to said tooth-simulating member and extending outwardly therefrom substantially at right angles to the major axis thereof, said pin extending through said mounting member and having the free end thereof projecting outwardly therefrom, said mounting means further including locking means on said free end of said pin operable to lock said tooth-simulating member and said mounting member in the assembled condition thereof.

4. The tooth shade guide member as set forth in claim 1 wherein said cover means comprises a cap dimensioned and configured to snugly fit over said front face of said tooth-simulating member, said cap snap fitting over said front face of said tooth-simulating member.

5. The tooth shade guide member as set forth in claim 4 wherein said cap includes a tab extending therefrom and formed integrally therewith, said tab being operable for use in dismounting said cap from said front face of said tooth-simulating member, and for receiving thereon identifying means operable for distinguishing said cap from another cap.

6. The tooth shade guide member as set forth in claim 1 wherein said cover means comprises dimensioned and configured to overlie said front face of said tooth-simulating member, said covering being detachably mounted on said front face of said tooth-simulating member by interposed pressure sensitive adhesive.

7. A tooth shade guide member operable for use by a dentist in determining by comparison the particular shade of an artificial tooth that may be substituted for a natural tooth of a patient comprising:

a. a tooth-simulating member having at least a front face dimensioned and configured to provide the appearance of a natural tooth, said tooth-simulating member being formed of a non-toxic material and having a preselected visible coloration;
b. an elongated mounting member formed of a non-toxic material and generally rectangular in configuration;
c. means pivotably mounting said tooth-simulating member on said mounting member adjacent to one end thereof and for pivotal movement relative thereto; and
d. a translucent disposable cap dimensioned and configured to snugly fit over said front face of said tooth-simulating member, said cap being formed of a non-toxic material transmitting light therethrough, said cap being detachably mounted on said front face of said tooth-simulating member having a coloration effective to alter said visible coloration of said tooth-simulating member so as to produce a variation in the shade of the apparent coloration of said tooth-simulating member from that seen when said cap is dismounted from said front face of said tooth-simulating member.

8. A tooth shade guide member operable for use by a dentist in determining by comparison the particular shade of an artificial tooth that may be substituted for a natural tooth of a patient comprising:

a. a tooth-simulating member having at least a front face dimensioned and configured to provide the appearance of a natural tooth, said tooth-simulating member being formed of a non-toxic material and having a preselected visible coloration;
b. an elongated mounting member formed of a non-toxic material and generally rectangular in configuration;
c. means pivotably mounting said tooth-simulating member on said mounting member adjacent to one end thereof and for pivotal movement relative thereto; and
d. a translucent covering dimensioned and configured to overlie said front face of said tooth-simulating member, said covering being formed of a non-toxic material transmitting light therethrough, said covering being detachably mounted on said front face of said tooth-simulating member by interposed pressure sensitive adhesive, said covering when mounted on said front face of said tooth-simulating member effective to alter the visible coloration of said tooth-simulating member so as to produce a variation in the shade of the apparent coloration of said tooth-simulating member from that seen when said covering is dismounted from said front face of said tooth-simulating member.

* * * * *